United States Patent [19]

Lautenschläger et al.

[11] Patent Number: 4,610,979

[45] Date of Patent: Sep. 9, 1986

[54] O-ACYL-ALKANEDIOL-PHOSPHOLIPIDS AND PROCESSES FOR THE TREATMENT OF ASTHMA

[75] Inventors: Hans-Heiner Lautenschläger, Pulheim; Erich Graf, Kerpen-Horrem; Sigurd Leyck, Pulheim, all of Fed. Rep. of Germany

[73] Assignee: A. Nattermann & Cie GmbH, Cologne, Fed. Rep. of Germany

[21] Appl. No.: 584,103

[22] Filed: Feb. 27, 1984

[30] Foreign Application Priority Data

Mar. 5, 1983 [DE] Fed. Rep. of Germany ....... 3307925

[51] Int. Cl.$^4$ .................. A61K 31/685; C07F 9/09
[52] U.S. Cl. ...................... 514/77; 558/169; 558/172
[58] Field of Search .......... 260/925; 424/199; 558/169, 172; 514/77

[56] References Cited

U.S. PATENT DOCUMENTS 4,493,832  1/1985  Teraji et al. .................. 424/199

OTHER PUBLICATIONS

Hach's Chemical Dictionary, (1969), p. 27.
Thuong et al., "Bull. Sco. Chim. Fr." (1974), p. 667.
Zeidler, "Fette, Seifen, Anstrichmittel", 83 (2), 57 (1981).
Eibl, "Phospholipid Synthesis" in Knight (publisher) Lipsomes, Elsevier (1981), pp. 34–35.
Mangold, "Agnew. Chem." 92, 550–560 (1979).
Eibl, "Chem. and Phys. of Lipids" 26, 405–429 (1980).
Chandrakumar et al., "Tetrahedron Lett." 23, 1043 (1982).

Primary Examiner—Anton H. Sutto
Attorney, Agent, or Firm—Pearne, Gordon, Sessions, McCoy, Granger & Tilberry

[57] ABSTRACT

The invention relates to new O-acyl-alkanediol-phospholipids of the general formula I

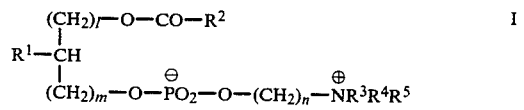

processes for their preparation and process for the treatment of certain diseases in humans.

6 Claims, No Drawings

O-ACYL-ALKANEDIOL-PHOSPHOLIPIDS AND PROCESSES FOR THE TREATMENT OF ASTHMA

The present invention relates to new O-acyl-alkanediol-phospholipids and processes for the treatment of certain diseases in human beings, such as for the treatment of asthma.

The O-acyl-alkanediol-phospholipids of the invention correspond to the general formula I

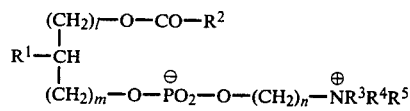

wherein $R^1$ signifies a saturated or unsaturated (preferably by one olefine double bond), straight or branched chain alkyl residue with 10 to 20 carbon atoms, $R^2$ signifies hydrogen, a straight or branched chain alkyl or alkoxy residue with 1 to 4 carbon atoms or a group $NR^6R^7$. The residues $R^3$, $R^4$, $R^5$ may be the same or different and represent a lower alkyl residue with 1 to 4 carbon atoms, preferably methyl. The residues $R^6$, $R^7$ may be the same or different and signify hydrogen, or a saturated or unsaturated (preferably by one olefine double bond), alkyl residue with 1 to 20 carbon atoms, phenyl, phenyl substituted by $C_{1-3}$-alkyl, $C_{1-3}$-alkoxy, halogen, or trifluoromethyl, or signify an aralkyl residue, especially the benzyl group. The indices l and m are 0. The index n is a whole number from 2 to 4, preferably 2.

Examples of compounds of the invention are:
1-O-acetyl-1.2-eicosandiol-2-O-phosphocholine
2-O-acetyl-1.2-octadecandiol-1-O-phosphocholine
1-O-acetyl-1.2-octadecandiol-2-O-phosphocholine
2-O-acetyl-1.2-dodecandiol-1-O-phosphocholine
2-O-acetyl-1.2-tetradecandiol-1-O-phosphocholine
2-O-acetyl-1.2-hexadecandiol-1-O-phosphocholine
2-O-acetyl-1.2-eicosandiol-1-O-phosphocholine
2-O-acetyl-1.2-docosandiol-1-O-phosphocholine
1-O-acetyl-1.2-dodecandiol-2-O-phosphocholine
1-O-acetyl-1.2-tetradecandiol-2-O-phosphocholine
1-O-acetyl-1.2-hexadecandiol-2-O-phosphocholine
1-O-acetyl-1.2-docosandiol-2-O-phosphocholine
2-O-formyl-1.2-eicosandiol-1-O-phosphocholine
2-O-propionyl-1.2-eicosandiol-1-O-phosphocholine
2-O-butyryl-1.2-eicosandiol-1-O-phosphocholine
(2-acetoxy-octadecyl)-triethylammonioethyl phosphate
(2-acetoxy-octadecyl)-tripropylammonioethyl phosphate
(2-acetoxy-octadecyl)-tributylammonioethyl phosphate
(2-acetoxy-octadecyl)-dimethylammonioethyl phosphate
3-O-acetyl-2-octadecyl-1.3-propandiol-1-O-phosphocholine
3-O-acetyl-2-decyl-1.3-propandiol-1-O-phosphocholine
3-O-acetyl-2-dodecyl-1.3-propandiol-1-O-phosphocholine
3-O-acetyl-2-tetradecyl-1.3-propandiol-1-O-phosphocholine
3-O-acetyl-2-hexadecyl-1.3-propandiol-1-O-phosphocholine
3-O-acetyl-2-eicosyl-1.3-propandiol-1-O-phosphocholine
(2-acetoxymethyl-eicosyl)-trimethylammoniopropyl phosphate
(2-acetoxymethyl-eicosyl)-trimethylammoniobutyl phosphate
(2-acetoxymethyl-eicosyl)-dimethylammonioethyl phosphate
1-O-methylcarbamoyl-1.2-octadecandiol-2-O-phosphocholine
1-O-ethylcarbamoyl-1.2-octadecandiol-2-O-phosphocholine
1-O-benzylcarbamoyl-1.2-octadecandiol-2-O-phosphocholine
1-O-carbamoyl-1.2-octadecandiol-2-O-phosphocholine
2-O-methylcarbamoyl-1.2-octadecandiol-1-O-phosphocholine
2-O-ethylcarbamoyl-1.2-octadecandiol-1-O-phosphocholine
1-O-ethylcarbamoyl-1.2-eicosandiol-2-O-phosphocholine
1-O-methylcarbamoyl-1.2-eicosandiol-2-O-phosphocholine
1-O-benzylcarbamoyl-1.2-eicosandiol-2-O-phosphocholine
1-O-carbamoyl-1.2-eicosandiol-2-O-phosphocholine
3-O-methylcarbamoyl-2-octadecyl-1.3-propandiol-1-O-phosphocholine
3-O-ethylcarbamoyl-2-octadecyl-1.3-propandiol-1-O-phosphocholine
2-O-methylcarbamoyl-1.2-dodecandiol-1-O-phosphocholine
2-O-ethylcarbamoyl-1.2-dodecandiol-1-O-phosphocholine
2-O-methylcarbamoyl-1.2-tetradecandiol-1-O-phosphocholine
2-O-ethylcarbamoyl-1.2-tetradecandiol-1-O-phosphocholine
2-O-methylcarbamoyl-1.2-hexadecandiol-1-O-phosphocholine
2-O-ethylcarbamoyl-1.2-hexadecandiol-1-O-phosphocholine
2-O-methylcarbamoyl-1.2-eicosandiol-1-O-phosphocholine
2-O-ethylcarbamoyl-1.2-eicosandiol-1-O-phosphocholine
2-O-methylcarbamoyl-1.2-docosandiol-1-O-phosphocholine
2-O-ethylcarbamoyl-1.2-docosandiol-1-O-phosphocholine
1-O-methylcarbamoyl-1.2-dodecandiol-2-O-phosphocholine
1-O-ethylcarbamoyl-1.2-dodecandiol-2-O-phosphocholine
1-O-methylcarbamoyl-1.2-tetradecandiol-2-O-phosphocholine
1-O-ethylcarbamoyl-1.2-tetradecandiol-2-O-phosphocholine
1-O-methylcarbamoyl-1.2-hexadecandiol-2-O-phosphocholine
1-O-ethylcarbamoyl-1.2-hexadecandiol-2-O-phosphocholine
1-O-methylcarbamoyl-1.2-docosandiol-2-O-phosphocholine
1-O-ethylcarbamoyl-1.2-docosandiol-2-O-phosphocholine
2-O-phenylcarbamoyl-1.2-eicosandiol-1-O-phosphocholine
2-O-[(4-chlorophenyl)-carbamoyl]-1.2-eicosandiol-1-O-phosphocholine
2-O-hexadecylcarbamoyl-1.2-eicosandiol-1-O-phosphocholine 2-O-oleylcarbamoyl-1.2-eicosandiol-1-O-phosphocholine
2-decyl-3-O-methylcarbamoyl-1.3-propandiol-1-O-phosphocholine
2-dodecyl-3-O-methylcarbamoyl-1.3-propandiol-1-O-phosphocholine
3-O-methylcarbamoyl-2-tetradecyl-1.3-propandiol-1-O-phosphocholine
2-hexadecyl-3-O-methylcarbamoyl-1.3-propandiol-1-O-phosphocholine
2-eicosyl-3-O-methylcarbamoyl-1.3-propandiol-1-O-phosphocholine
2-decyl-3-O-ethylcarbamoyl-1.3-propandiol-1-O-phosphocholine
2-dodecyl-3-O-ethylcarbamoyl-1.3-propandiol-1-O-phosphocholine
3-O-ethylcarbamoyl-2-tetradecyl-1.3-propandiol-1-O-phosphocholine
3-O-ethylcarbamoyl-2-hexadecyl-1.3-propandiol-1-O-phosphocholine
2-eicosyl-3-O-ethylcarbamoyl-1.3-propandiol-1-O-phosphocholine
2-O-dimethylcarbamoyl-1.2-octadecandiol-1-O-phosphocholine
2-O-dimethylcarbamoyl-1.2-dodecandiol-1-O-phosphocholine
2-O-dimethylcarbamoyl-1.2-tetradecandiol-1-O-phosphocholine
2-O-dimethylcarbamoyl-1.2-hexadecandiol-1-O-phosphocholine
2-O-dimethylcarbamoyl-1.2-eicosandiol-1-O-phosphocholine
2-O-dimethylcarbamoyl-1.2-docosandiol-1-O-phosphocholine
1-O-dimethylcarbamoyl-1.2-dodecandiol-2-O-phosphocholine
1-O-dimethylcarbamoyl-1.2-tetradecandiol-2-O-phosphocholine
1-O-dimethylcarbamoyl-1.2-hexadecandiol-2-O-phosphocholine
1-O-dimethylcarbamoyl-1.2-octadecandiol-2-O-phosphocholine
1-O-dimethylcarbamoyl-1.2-eicosandiol-2-O-phosphocholine
1-O-dimethylcarbamoyl-1.2-docosandiol-2-O-phosphocholine
2-decyl-3-O-dimethylcarbamoyl-1.3-propandiol-1-O-phosphocholine
3-O-dimethylcarbamoyl-2-dodecyl-1.3-propandiol-1-O-phosphocholine
3-O-dimethylcarbamoyl-2-tetradecyl-1.3-propandiol-1-O-phosphocholine
3-O-dimethylcarbamoyl-2-hexadecyl-1.3-propandiol-1-O-phosphocholine
3-O-dimethylcarbamoyl-2-octadecyl-1.3-propandiol-1-O-phosphocholine
3-O-dimethylcarbamoyl-2-eicosyl-1.3-propandiol-O-phosphocholine O-Carbamoyl-alkandiol-phospholipids of the present invention are prepared by reacting lyso-phospholipids of the formula II

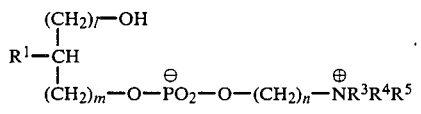

in which $R^1$, $R^3$, $R^4$, $R^5$, l, m, n have the meanings given in formula I, with carbonic acid derivatives of the formula III or IV

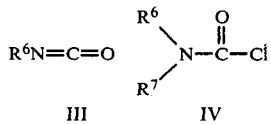

in which $R^6$ and $R^7$ have the meanings given in formula I, in an inert organic solvent, e.g. chloroform, dimethyl formamide, N-methyl acetamide, with optional addition of a catalyst or a base such as dimethylaminopyridine, pyridine, triethylamine, silver carbonate, barium carbonate, especially when using compounds of the formula IV.

Compounds of the formula I with $R^6=R^7=H$ can be prepared advantageously by hydrogenating, with hydrogen, compounds of the formula I with $R^6$=benzyl and $R^7$=H in a suitable organic solvent, e.g. methanol, ethanol, ether, dioxan or mixtures thereof with each other and with water, with splitting-off of the benzyl group in the presence of a conventional hydrogenation catalyst, e.g. palladium/active carbon.

Examples of useful starting compounds of the formula II are:
1.2-Dodecandiol-1-O-phosphocholine
1.2-tridecandiol-1-O-phosphocholine
1.2-tetradecandiol-1-O-phosphocholine
1.2-pentadecandiol-1-O-phosphocholine
1.2-hexadecandiol-1-O-phosphocholine
1.2-heptadecandiol-1-O-phosphocholine
1.2-octadecandiol-1-O-phosphocholine
1.2-nonadecandiol-1-O-phosphocholine
1.2-eicosandiol-1-O-phosphocholine
1.2-heneicosandiol-1-O-phosphocholine
1.2-docosandiol-1-O-phosphocholine
1.2-dodecandiol-2-O-phosphocholine
1.2-tridecandiol-2-O-phosphocholine
1.2-tetradecandiol-2-O-phosphocholine
1.2-pentadecandiol-2-O-phosphocholine
1.2-hexadecandiol-2-O-phosphocholine
1.2-heptadecandiol-2-O-phosphocholine
1.2-octadecandiol-2-O-phosphocholine
1.2-nonadecandiol-2-O-phosphocholine
1.2-eicosandiol-2-O-phosphocholine
1.2-heneicosandiol-2-O-phosphocholine
1.2-docosandiol-2-O-phosphocholine
2-decyl-1.3-propandiol-1-O-phosphocholine
2-undecyl-1.3-propandiol-1-O-phosphocholine
2-dodecyl-1.3-propandiol-1-O-phosphocholine
2-tridecyl-1.3-propandiol-1-O-phosphocholine
2-tetradecyl-1.3-propandiol-1-O-phosphocholine
2-pentadecyl-1.3-propandiol-1-O-phosphocholine
2-hexadecyl-1.3-propandiol-1-O-phosphocholine
2-heptadecyl-1.3-propandiol-1-O-phosphocholine
2-octadecyl-1.3-propandiol-1-O-phosphocholine
2-nonadecyl-1.3-propandiol-1-O-phosphocholine
2-eicosyl-1.3-propandiol-1-O-phosphocholine
2-oleyl-1.3-Propandiol-1-O-phosphocholine
2-linoleyl-1.3-propandiol-1-O-phosphocholine
2-(15-methyl-hexadecyl)-1.3-propandiol-1-O-phosphocholine
2-(17-methyl-octadecyl)-1.3-propandiol-1-O-phosphocholine, the lyso-compounds being usable in either their R- or their S-form or as a racemic mixture.

Examples of starting compounds of the formula III are: Methyl isocyanate, ethyl isocyanate, propyl isocyanate, isopropyl isocyanate, butyl isocyanate, allyl isocyanate, hexyl isocyanate, octyl isocyanate, decyl isocyanate, undecyl isocyanate, dodecyl isocyanate, tetradecyl isocyanate, hexadecyl isocyanate, octadecyl isocyanate, eicosyl isocyanate, oleyl isocyanate, linoleyl isocyanate, phenyl isocyanate, 4-chlorophenyl isocyanate, 3-fluorophenyl isocyanate, 4-fluorophenyl isocyanate, p-tolyl isocyanate, p-methoxyphenyl isocyanate, p-trifluoromethyl isocyanate, m-trifluoromethyl isocyanate, benzyl isocyanate.

Preferred examples of the starting compounds of the formula IV are carbamic acid chlorides whose substituents $R^6$, $R^7$ contain a short-chain hydrocarbon residue with 1-4 carbon atoms, e.g. dimethylcarbamic acid chloride, diethylcarbamic acid chloride, dipropylcarbamic acid chloride, dibutylcarbamic acid chloride, methylethylcarbamic acid chloride, methylpropylcarbamic acid chloride, methylbutylcarbamic acid chloride, ethylpropylcarbamic acid chloride, butylpropylcarbamic acid chloride, butylethylcarbamic acid chloride.

O-Alkanoyl- and O-alkoxycarbonyl-alkanediol-phospholipids according to the present invention are likewise prepared from the lyso-compound of the formula II, by reacting the latter with the corresponding alkanoic acid halides, alkanoic acid anhydrides or chloroformic acid esters of the formula V $$X-CO-R^2 \qquad V$$

in which X is any halogen, preferably chlorine, or the residue $R^2-CO-O-$ (anhydrides) and $R^2$ signifies a straight or branched chain alkyl or alkoxy residue according to formula I, in an inert organic solvent, e.g. chloroform, dimethylformamide, with optional addition of an acid acceptor, e.g. pyridine, triethylamine.

Examples of starting compounds of the formula V are: Acetyl chloride, propionyl chloride, butyryl chloride, isobutyryl chloride, acetic anhydride, propionic anhydride, butyric anhydride, isobutric anhydride, methyl chlorformate, ethyl chloroformate, propyl chloroformate, isopropyl chloroformate, butyl chloroformate, isobutyl chloroformate.

In the case where $R^2=H$, mixed anhydrides, e.g. formic/acetic anhydride can also be used.

O-Acyl-alkandiol-phospholipids of the general formula I are also available from alcohols of the formula VI

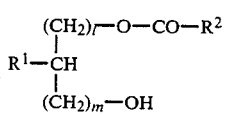
VI in which $R^1$, $R^2$, l, m have the meanings given in formula I, by reacting them with dichlorophosphoric acid ω-halo-alkanoic acid esters of the formula VII

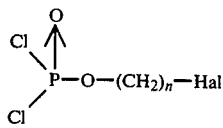
VII in which has the meaning given in formula I and Hal is a chlorine or bromine atom, in an inert organic solvent, with optional use of an auxiliary base e.g. pyridine or triethylamine, and subsequently treating with an amine of the formula VIII

VIII in which $R^3, R^4$ and $R^5$ have the meanings given in formula I, in an inert organic solvent e.g. toluene, dioxan, tetrahydrofuran, optionally under pressure. Cf in this connection H K Mangold, Angew. Chem. 92, 550–560 (1979); H. Eibl, Chem. and Phys. of Lipids 26, 405–429 (1980).

The compounds of formula I can also be prepared by phosphorylating compounds of the formula VI with phosphorus oxytrichloride, and afterwards reacting with an alkandiol of the formula IX $$HO-(CH_2)_n-OH \qquad IX$$

in which n has the meaning given in formula I, with optional use of auxiliary bases e.g. triethylamine, and with use of inert solvents e.g. tetrahydrofuran, to yield cyclic intermediates of the formula X

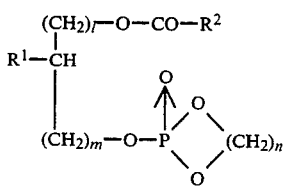
X in which $R^1$, $R^2$, l, m, n have the meanings given in formula I. Cf H. Eibl, Phospholipid Synthesis in Knight (Publisher) Liposomes, Elsevier 1981, pp 19–50. The intermediates of the formula X can also be prepared by reacting compounds of the formula VI with a cyclic phosphorus compound of the formual XI

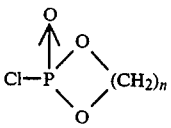
XI in which n has the meaning given in formula I, in an inert organic solvent with addition of an auxiliary base. Cf N. S. Chandrakumar et al., Tetrahedron Lett. 23, 1043 (1982); Biochim. Biophys. Acta 711, 357 (1982). The intermediates X can be converted in a simple manner into the compounds of the formula I, e.g. by treatment with an amine of the formula VIII, in an organic solvent, optionally under pressure. Cf N. T. Thuong and P. Chabrier, Bull. Soc. Chim. Fr. 1974, 667 ff.

Examples of starting compounds of the formula VII are: Dichlorophosphoric acid 2-bromoethyl ester, dichlorophosphoric acid 2-chloroethyl ester, dichlorophosphoric acid 3-bromopropyl ester, dichlorophosphoric acid 4-bromobutyl ester.

Preferred starting compounds of the formula VIII are secondary and tertiary amines, e.g. dimethylamine, diethylamine, dipropylamine, dibutylamine, trimethylamine, triethylamine, tripropylamine, tributylamine, ethylmethylamine, methylpropylamine, ethylpropylamin, butylmethylamine, butylethylamine, butylpropylamine, dimethylethylamine, dimethylpropylamine, butyldimethylamine, diethylmethylamine, diethylpropylamine, butyldiethylamine, dipropylmethylamine, dipropylethylamine, butyldipropylamine, dibutylmethylamine, dibutylethylamine, dibutylpropylamine, ethylmethylpropylamine, butylmethylpropylamine, butylethylmethylamine, butylethylpropylamine.

The lyso-compounds with $l=1$ and $m=0$, used as starting compounds of the formula II are prepared by reacting epoxides of the formula XII

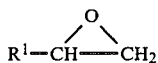
XII in which $R^1$ has the meaning given in formula I, in the form of the pure substance or dissolved in an inert organic solvent, with benzyl alcohol or a comparable protecting group reagent in the presence of a base, preferably at temperatures of 0°–150° C., to yield a 1-O-protected diol of the formula XIII

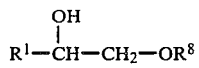
XIII

Apart from benzyl or a comparable protecting group, the residue $R^8$, in a special case, can also be trityl or substituted trityl, if XIII is prepared by the conventional procedure from the original diol and trityl halides or substituted trityl halides. For their part the compounds XIII are transformed into the phospholipids of the formula XIV

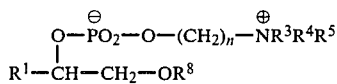
XIV anologously to the previously described phosphorylation procedure. The compounds XIV are hydrogenated with hydrogen in a suitable organic solvent, e.g. methanol, ethanol, ether, dioxan or mixtures thereof with each other and with water, with splitting-off of the benzyl or trityl group in the presence of one of the conventional hydrogenation catalysts, e.g. palladium/active carbon, yielding the desired lyso-compounds II with $l=1$ and $m=0$. In the case where $R^8$=trityl or substituted trityl, the conventional ether scissions can be carried out with the aid of organic or inorganic acids in aqueous/organic media.

The lyso-compounds with $l=0$ and $m=1$, used as starting compounds of the formula II, are prepared from the compounds XIII, by converting the latter into the acyl derivatives XV

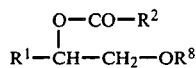
XV in which $R^2$ has the meaning given in formula I and $R^8$ that given in formula XIII, by means of a reactive acid derivative, e.g. an acid halide or anhydride, optionally in the presence of an acid acceptor such as triethylamine, pyridine, inorganic oxides, carbonates etc. The acyl derivatives XV are hydrogenated with hydrogen in a suitable organic solvent, e.g. methanol, ethanol, ether, dioxan or mixtures thereof with each other and with water, with splitting-off of the benzyl or trityl group in the presence of one of the conventional hydrogenation catalysts, e.g. palladium/active carbon, yielding compounds of the formula XVI

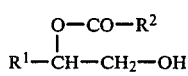
XVI

The compounds of the formula XVI are converted into the phospholipids of the formula I with $R^2$=hydrogen, alkyl, alkoxy analogously to the previously described processes for the phosphorylation of VI, and the phospholipids, if desired, are converted by mild alkaline hydrolysis to the lyso-compounds of the formula II with $l=0$ and $m=1$.

The lyso-compounds with $l=1$ and $m=1$, used as starting compounds of the formula II, are prepared by reducing substituted malonic acid diesters of the formula XVII

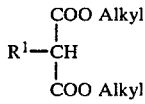
XVII in which $R^1$ has the meaning given in formula I and Alkyl represents a suitable alkyl residue, preferably methyl or ethyl, with an appropriate reducing agent e.g. lithium aluminium hydride, to yield the diols of the formula XVIII

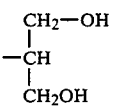
XVIII

The diols XVIII can, just like the diols of the formula XIX

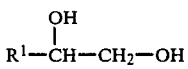
XIX in which $R^1$ likewise has the meaning given in formula I, be converted directly into the lyso-compounds II with $l=m=1$ or $l=0$, $m=1$, analogously to the previously described process for the phosphorylation of VI.

On the other hand the compound XVIII can also be converted with benzyl halides or similar protecting group reagents by the conventional methods to the monobenzyl ethers XX

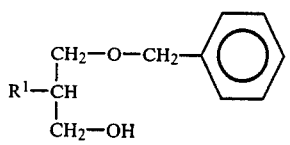

XX from which—analogously to the processes previously described for the phosphorylation of VI—the phospholipids XXI can be obtained

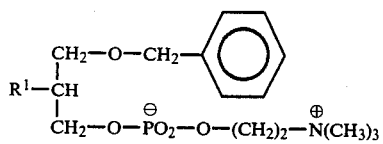

XXI

The phospholipids XXI yield the lyso-compounds of the formula II with $l=m=1$, analogously to the hydrogenation or scission of a similar protecting group described for the preparation of XVI from XV.

Phospholipids of the formula I with $R^2$=hydrogen or alkyl and $l=1$ as well as $m=0$ can also be prepared by opening epoxides of the formula XII with the corresponding acids $R^2COOH$ to yield the ester-alcohols XXII

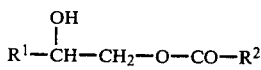

XXII according to the procedure given by U. Zeidler in Fette, Seifen, Anstrichmittel 83 (2), 57 (1981), and treating said ester-alcohols similarly to the process described for the phosphorylation of VI.

The present invention relates likewise to processes for the treatment of certain diseases in humans wherein a compound according to formula I is administered to a human being suffering from such diseases in the dosages given below. The compounds of formula I are administered in the form of pharmaceutical preparations for enteral, oral, rectal as well as parenteral administration, and they contain the pharmaceutical active ingredients alone or together with a conventional pharmaceutically usable carrier material. Advantageously the pharmaceutical presentation of the active ingredient is in the form of single doses, which are adapted to the desired mode of administration, e.g. tablets, dragees, capsules, suppositories, granulates, solutions, emulsions or suspensions. The dosage of the compounds of formula I lies normally between 1 and 1000 mg per dose, preferably between 1 to 10 mg per dose, and can be administered once or oftener, preferably 2 to 3 times daily.

The preparation of the compounds of the invention is described in more detail by the following examples. The melting points given were measured with a Buechi 510 melting point determination apparatus and are uncorrected.

EXAMPLE 1

1-O-Acetyl-1.2-eicosandiol-2-O-phosphocholine.

(a) 1-O-Acetyl-1.2-eicosandiol.

95 g of 1.2-Epoxyeicosane is mixed with 21 g of acetic acid and about 0.1 g of sodium acetate and the mixture stirred for 6 hours at 130° C. The mixture is evaporated and the residue purified by column chromatography (silica gel/chloroform).

Yield: 74 g; Mp: 73° C.

(b) (1-Acetoxymethyl-nonadecyl)-2-bromoethyl phosphate.

13 g of 1-O-acetyl-1.2-eicosandiol is dissolved in 200 ml of pyridine and 17.7 g of 2-bromoethylphosphoric acid dichloride are added dropwise with ice cooling. After about 2 hours of stirring at room temperature, 200 ml of water are added and the mixture further stirred for half an hour at room temperature. After dilution with water, it is extracted with chloroform, the chloroform phase is washed with water and dried over sodium sulphate. After evaporation of the solvent in vacuo the residue is purified by column chromatograph (silica gel//chloroform/methanol).

Yield: 10.4 g (oil).

(c) 1-O-Acetyl-1.2-eicosandiol-2-O-phosphocholine.

9 g of (1-acetoxymethyl-nonadecyl)-2-bromoethyl phosphate is dissolved in 100 ml of toluene, 15 ml of 20% trimethylamine solution in toluene is added and the mixture stirred for 5 hours at 60° C. in the autoclave. After evaporation of the solvent in vacuo the residue is purified by column chromatography (silica gel//chloroform/methanol).

Yield: 4.2 g; Mp 194°–197° C.

EXAMPLE 2

2-O-Acetyl-1.2-octadecandiol-1-O-phosphocholine.

(a) 1-O-Benzyl-1.2-octadecandiol.

216 g of benzyl alcohol is added dropwise to a suspension of 9.8 g of sodium hydride in toluene at boiling point. When the evolution of hydrogen has ceased the mixture is cooled and, one after the other, 268 g of 1.2-epoxyoctadecane and 2.73 g of 18-Krone-6 are added. The mixture is stirred at 60° C. to the end of the reaction, cooled, washed with water and dried over magnesium sulphate. After removal of the excess benzyl alcohol and solvent the residue is purified by column chromatography (silica gel/chloroform).

Yield: 302 g; Mp: 48° C.

(b) 2-O-Acetyl-1-O-benzyl-1.2-octadecandiol.

89 g of 1-O-benzyl-1.2-octadecandiol is reacted with 48 g of acetic anhydride and the mixture heated under reflux for 1 hour. After removal of the excess acetic anhydride and acetic acid in vacuo the residue is further worked up directly.

Yield: 97 g (oil).

(c) 2-O-Acetyl-1.2-octadecandiol.

15 g of 2-O-acetyl-1-O-benzyl-1.2-octadecandiol is dissolved in 50 ml of ethanol, the solution is then hydrogenated with hydrogen at 0° C. for 4 hours after addition of 1.5 g of palladium/active carbon. The active carbon is filtered off and the filtrate cooled to −20° C. The precipitated solid is filtered off and dried in a high vacuum.

Yield: 9.1 g; Mp: 46° to 49° C.

(d) (2-Acetoxy-octadecyl)-2-bromoethyl phosphate.

6 g of 2-O-acetyl-1.2-octadecandiol is dissolved in 100 ml of choroform and, one after the other, 8 ml of pyridine and 6.6 g of 2-bromoethylphosphoric acid dichloride are added at 0° C. After stirring for 1 hour with ice cooling and addition of a little ice water, the mixture is again stirred for half an hour at 0° C. The organic phase is separated, washed with water and dried over sodium sulphate. After evaporation of the solvent in vacuo the residue is purified by column chromatography (silica gel//chloroform/methanol).

Yield: 5.2 g (oil).

(e) 2-O-Acetyl-1.2-octadecandiol-1-O-phosphocholine.

3 g of (2-acetoxy-octadecyl)-2-bromoethyl phosphate is dissolved in 100 ml of toluene, 10 ml of 20% trimethylamine solution in toluene is added to the solution, and the mixture is stirred for 5 hours at 60° C. in the autoclave. After evaporation of the solvent in vacuo the residue is purified by column chromatography (silica gel//chloroform/methanol).

Yield: 2.1 g; Mp: 228° C.

EXAMPLE 3

1-O-Acetyl-1.2-octadecandiol-2-O-phosphocholine.

(a) (1-Acetoxymethyl-heptadecyl)-2-bromoethyl phosphate.

70 g of 1-O-acetyl-1.2-octadecandiol (prepared similarly to 1-O-acetyl-1.2-eicosandiol) are dissolved in 400 ml of pyridine and 77 g of 2-bromoethyl phosphoric acid dichloride are added dropwise with ice cooling. After about 2 hours of stirring at room temperature 400 ml of water are added and the mixture further stirred for half an hour at room temperature. After dilution with water the mixture is extracted with chloroform, the chloroform phase washed with 5% hydrochloric acid and water, dried over sodium sulphate and the solvent removed. The crude product (110 g) is worked up further without purification.

(b) 1-O-Acetyl-1.2-octadecandiol-2-O-phosphocholine.

110 g of (1-acetoxymethyl-heptadecyl)-2-bromoethyl phosphate (crude product) are dissolved in 500 ml of toluene, 300 ml of 20% trimethylamine solution in toluene are added and the mixture stirred for 8 hours at 60° C. in the autoclave. After evaporation of the solvent in vacuo the residue is purified by column chromatography (silica gel//chloroform/methanol).

Yield: 50.5 g; Mp: 217° to 224° C.

EXAMPLE 4

1-O-Acetyl-1.2-octadecandiol-2-O-phosphocholine (from 1.2-octadecandiol-2-O-phosphocholine).

1 g of 1.2-octadecandiol-2-O-phosphocholine is dissolved in 20 ml of chloroform and 0.7 g of acetic anhydride are added. The mixture is stirred until the reaction is complete, evaporated to dryness in vacuo and the residue is freeze-dried after dissolving in water.

Yield: 1.1 g; Mp: 218° to 225° C.

EXAMPLE 5

3-O-Acetyl-2-octadecyl-1.3-propandiol-1-O-phosphocholine.

(a) 2-Octadecylmalonic acid diethyl ester.

One after the other, 160 g of diethyl malonate and 350 g of bromo octadecane are added dropwise to a hot solution of 23 g of sodium hydroxide in 500 ml of absolute ethanol, and the mixture heated under reflux for about 12 hours, until the solution gives a nearly neutral reaction. Then the solvent is removed, the residue shaken with water and ether, the ether phase dried over sodium sulphate and the ether evaporated. The residual oil is distilled in vacuo.

Yield: 311 g ($Kp_{0.2\,mm}$ 195° to 200° C.); Mp: 39° to 41° C.

(b) 2-Octadecyl-1.3-propandiol.

150 g of diethyl 2-octadecylmalonate are dissolved in 200 ml of absolute tetrahydrofuran and the solution slowly added dropwise to 14 g of lithium aluminium hydride in 300 ml of tetrahydrofuran. The mixture is boiled for 4 hours under reflux, reacted with isopropanol with ice cooling and thereafter with 10% sulfuric acid, until the precipitate of aluminium hydroxide just redissolves. The greater part of the solvent is removed in vacuo and the residue treated with chloroform. 2-Octadecyl-1.3-propandiol precipitates from the chloroform phase and is filtered off and dried.

Yield: 248 g; Mp: 88° C.

(c) 2-Benzyloxymethyl-eicosanol.

110 g of 2-octadecyl-1.3-propandiol are added at 80° C. to a suspension of 16 g of sodium hydride in 1.5 l of dimethylformamide. When hydrogen evolution has finished, 42 g of benzyl chloride dissolved in 500 ml of dimethylformamide are added dropwide with strong agitation. The mixture is stirred for 8 hours at 80° C., the solvent substantially removed in vacuo and water added. Thereupon the mixture is extracted with chloroform, the chloroform phase washed with water and dried over sodium sulphate. After removal of the solvent the residue is stirred with hexane, unreacted starting substance is filtered off and the filtrate is evaporated. The residue from the filtrate is purified by column chromatography (silica gel//hexane/ethyl acetate).

Yield: 76 g.

(d) (2-Benzyloxymethyl-eicosyl)-2-bromoethyl phosphate.

20 g of 2-benzyloxymethyl-eicosanol, dissolved in a little of chloroform, is added dropwise to an ice-cooled mixture of 17 g of 2-bromoethylphosphoric acid dichloride, 8 ml of pyridine and 200 ml of chloroform. The mixture is stirred for 5 hours, treated with 200 ml of water and stirred again for half an hour. The organic phase is separated, washed with water and dried over sodium sulphate. The solvent is removed and the residue is purified by column chromatography (silica gel//chloroform/methanol).

Yield: 17.5 g (oil).

(e) 3-O-Benzyl-2-octadecyl-1.3-propandiol-1-O-phosphocholine.

17.5 g of (2-benzyloxymethyl-eicosyl)-2-bromoethyl phosphate is dissolved in 150 ml of toluene, 20 ml of 33% alcoholic trimethylamine solution is added and the mixture stirred for 5 hours at 70° C. After evaporation of the solvent in vacuo the residue is purified by column chromatography (silica gel//chloroform/methanol).

Yield: 12 g; Mp: 237° to 242° C.

(f) 2-Octadecyl-1.3-propandiol-1-O-phosphocholine.

15 g of 3-O-benzyl-2-octadecyl-1.3-propandiol-1-O-phosphocholine are dissolved in 300 ml of ethanol, the solution is hydrogenated with hydrogen after addition of 1.5 g of palladium/active carbon with gradual addition of about 100 ml of water. After the active carbon has been filtered off, the residue is evaporated and worked up further without purification.

Yield: 10.1 g; Mp: 240° C.

(g) 3-O-Acetyl-2-octadecyl-1.3-propandiol-1-O-phosphocholine.

1 g of 2-octadecyl-1.3-propandiol-1-O-phosphocholine is dissolved in 20 ml of chloroform and 5 ml of acetic anhydride is added. The mixture is stirred at 80° C. until reaction is complete, evaporated to dryness in vacuo and the residue is washed with acetone.

Yield: 10 g; Mp: 207° to 220° C.

EXAMPLE 6

1-O-Methylcarbamoyl-1.2-octadecandiol-2-O-phosphocholine.

(a) 1.2-Octadecandiol-2-O-phosphocholine.

10 g of 1-O-acetyl-1.2-octadecandiol-2-O-phosphocholine are dissolved in 100 ml of absolute ethanol and 2.8 g of potassium carbonate added. The mixture is stirred at room temperature for 24 hours, filtered and evaporated to dryness in vacuo. The residue is shaken up with acetone, the solid substance filtered off and dried.

Yield: 7.5 g; Mp: 273° C.

(b) 1-O-Methylcarbamoyl-1.2-octadecandiol-2-O-phosphocholine.

2 g of 1.2-octadecandiol-2-O-phosphocholine are dissolved in 20 ml of chloroform and 1 ml of dimethylformamide, and 0.5 g of methyl isocyanate are added dropwise. The mixture is stirred at room temperature for 24 hours, the solvent removed and the residue purified by column chromatography (silica gel//chloroform/methanol).

Yield: 1.2 g; Mp: about 240° C. (dec.).

EXAMPLE 7

1-O-ethylcarbamoyl-1.2-octadecandiol-2-O-phosphocholine.

2 g of 1.2-octadecandiol-2-O-phosphocholine are dissolved in 20 ml of chloroform and 1 ml of dimethylformamide, and 0.5 g of ethyl isocyanate are added. The mixture is stirred at room temperature for 24 hours, the solvent removed and the residue purified by column chromatograhy (silica gel//chloroform/methanol).

Yield: 1.3 g; Mp: 241° C.

EXAMPLE 8

1-O-Benzylcarbamoyl-1.2-octadecandiol-2-O-phosphocholine.

2 g of 1.2-octadecandiol-2-O-phosphocholine are dissolved in 20 ml of chloroform and 1 ml of dimethylformamide, and 1.2 g of benzyl isocyanate are added. The mixture is stirred of and the residue is purified by column chromatography (silica gel//chloroform/methanol)

Yield: 1.6 g; Mp: about 211° C. (dec.).

EXAMPLE 9

1-O-Carbamoyl-1.2-octadecandiol-2-O-phosphocholine.

Prepared similarly to 1-O-carbamoyl-1.2-eicosandiol-2-O-phosphocholine, from:
0.5 g of 1-O-benzylcarbamoyl-octadecandiol-2-O-phosphocholine,
50 ml of ethanol and
0.5 g of palladium/active carbon.
Yield: 160 mg; Mp: 236° C. (dec.).

EXAMPLE 10

2-O-Methylcarbamoyl-1.2-octadecandiol-1-O-phosphocholine.

(a) 1.2-Octadecandiol-1-O-phosphocholine.

1 g of 2-O-acetyl-1.2-octadecandiol-1-O-phosphocholine are dissolved in 10 ml of absolute ethanol, and 300 mg of potassium carbonate are added. The mixture is stirred at room temperature for 24 hours, filtered and evaporated to dryness in vacuo. The residue (0.8 g) is further processed without purification.

(b) 2-O-Methylcarbamoyl-1.2-octadecandiol-1-O-phosphocholine.

0.2 g of 1.2-octadecandiol-1-O-phosphocholine are dissolved in 10 ml of chloroform, and 10 drops of dimethylformamide plus 0.1 g of methyl isocyanate added. The mixture is stirred at room temperature for 48 hours, the solvent removed and the residue purified by column chromatography (silica gel//chloroform/methanol).

Yield: 0.12 g; Mp: 246° C. (dec.).

EXAMPLE 11

2-O-Ethylcarbamoyl-1.2-octadecandiol-1-O-phosphocholine.

0.2 g of 1.2-octadecandiol-1-O-phosphocholine are dissolved in 10 ml of chloroform, and 10 drops of dimethylformamide plus 0.1 g of ethyl isocyanate added. The mixture is stirred at room temperature for 48 hours, the solvent removed and the residue purified by column chromatography (silica gel//chloroform/methanol).

Yield: 0.1 g; Mp: 241° C.

EXAMPLE 12

1-O-Ethylcarbamoyl-1.2-eicosandiol-2-O-phosphocholine.

(a) 1.2-Eicosandiol-2-O-phosphocholine.

2 g of 1-O-acetyl-1.2-eicosandiol-2-O-phosphocholine are dissolved in 20 ml of absolute ethanol, and 530 mg of potassium carbonate added. The mixture is stirred at room temperature for 24 hours, filtered and evaporated to dryness in vacuo. The residue (1.9 g) is further processed without purification.

(b) 1-O-Ethylcarbamoyl-1.2-eicosandiol-2-O-phosphocholine.

0.5 g of 1.2-eicosandiol-2-O-phosphocholine are dissolved in 20 ml of chloroform, and 1 ml of dimethylformamide and 0.2 g of ethyl isocyanate added to the solution. The mixture is stirred for about 5 hours at room temperature, the solvent removed and the residue purified by column chromatography (silica gel//chloroform/methanol).

Yield: 0.3 g; Mp: 220° C.

EXAMPLE 13

1-O-Methylcarbamoyl-1.2-eicosandiol-2-O-phosphocholine.

0.5 g of 1.2-eicosandiol-2-O-phosphocholine are dissolved in 20 ml of chloroform, and 1 ml of dimethylformamide and 0.2 g of methyl isocyanate added to the mixture. The mixture is stirred at room temperature for about 5 hours, the solvent removed and the residue purified by column chromatography (silica gel//chloroform/methanol).

Yield: 0.23 g; Mp: 235° C. (dec.).

EXAMPLE 14

1-O-Benzylcarbamoyl-1.2-eicosandiol-2-O-phosphocholine.

0.5 g of 1.2-eicosandiol-2-O-phosphocholine are dissolved in 20 ml of chloroform, and 1 ml of dimethylformamide and 0.5 g of benzyl isocyanate added to the solution. The mixture is stirred at room temperature until reaction is complete, the solvent removed and the residue purified by column chromatography (silica gel//chloroform/methanol).

Yield: 0.5 g; Mp: 225° C. (dec.).

EXAMPLE 15

1-O-Carbamoyl-1.2-eicosandiol-2-O-phosphocholine.

0.4 g of 1-O-benzylcarbamoyl-1.2-eicosandiol-2-O-phosphocholine are dissolved in 50 ml of ethanol, the solution hydrogenated with hydrogen for 7 days with successive addition of a total of 0.4 g of palladium/active carbon and a little water. After filtering off the active carbon the filtrate is evaporated to dryness in vacuo, and the residue purified by column chromatography (silica gel//chloroform/methanol).

Yield: 0.30 g; Mp: 237° C. (dec.).

EXAMPLE 16

3-O-Methylcarbamoyl-2-octadecyl-1.3-propandiol-1-O-phosphocholine.

1 g of 2-octadecyl-1.3-propandiol-1-O-phosphocholine are dissolved in 20 ml of chloroform, and 10 ml of dimethylformamide and 10 ml of methyl isocyanate added to the solution. The mixture is stirred at 60° C. until reaction is complete, the solvent removed and the residue purified by column chromatography (silica gel//chloroform/methanol).

Yield: 0.42 g; Mp: 234° to 239° C.

EXAMPLE 17

3-O-Ethylcarbamoyl-2-octadecyl-1.3-propandiol-1-O-phosphocholine.

1 g of 2-octadecyl-1.3-propandiol-1-O-phosphocholine are dissolved in 20 ml of chloroform, and 10 ml of dimethylformamide and 10 ml of ethyl isocyanate added to the solution. The mixture is stirred at 60° C. until reaction is complete, the solvent removed and the residue purified by column chromatography (silica gel//chloroform/methanol).

Yield: 0.5 g; Mp: 209° to 218° C.

EXAMPLE 18

2-O-Dimethylcarbamoyl-1.2-octadecandiol-1-O-phosphocholine.

0.9 g of 1.2-octadecandiol-1-O-phosphocholine are dissolved in 50 ml of chloroform, the solution reacted with 0.43 g of dimethylcarbamic acid chloride and 0.6 g of silver carbonate, and stirred at room temperature for 12 hours. The solution is filtered and evaporated in vacuo and the residue purified by column chromatography (silica gel//chloroform/methanol).

Yield: 0.75 g; Mp: 221° C.

What we claim is:

1. O-Acyl-alkanediol-phospholipids of the general formula I

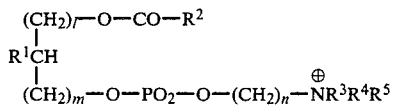

wherein $R^1$ is a member selected from the group consisting of the straight chain and branched chain alkyl groups having from 10 to 20 carbon atoms and the straight chain and the branched chain alkylene groups having from 10 to 20 carbon atoms, $R^2$ is a member selected from the group consisting of hydrogen, the straight chain and the branched chain alkyl groups having from 1 to 4 carbon atoms and the group $-NR^6R^7$, $R^3$, $R^4$ and $R^5$, which may be the same or different from each other, each are a member selected from the group consisting of hydrogen and the lower alkyl groups having from 1 to 4 carbon atoms, $R^6$ and $R^7$ which may be the same or different from each other, each represent member selected from the group consisting of alkyl groups having from 1 to 20 carbon atoms and alkylene groups having from 1 to 20 carbon atoms, the unsubstituted phenyl group, phenyl substituted by $C_{1-3}$-alkyl, $C_{1-3}$-alkoxy, halogen or trifluoromethyl, and the aralkyl groups, l and m, which may be the same or different from each other, represent 0 or 1 except that l and m may not both be zero, and m represents a whole number from 2 to 4.

2. O-Acyl-alkanediol-phospholipids as claimed in claim 1, wherein $R^2$ is a member selected from the group consisting of hydrogen, the straight chain alkyl groups having from 1 to 4 carbon atoms and the group $-NR^6R^7$, $R^3$, $R^4$ and $R^5$ each are a methyl group, $R^6$ and $R^7$, if an aralkyl group, is the benzyl group, and n is 2.

3. O-Carbamoyl-alkanediol-phospholipids as claimed in claim 1, wherein $R^1$ is a member selected from the group consisting of the straight chain and branched chain alkyl groups having 10 to 20 carbon atoms and the straight chain and the branched chain alkylene groups having from 10 to 20 carbon atoms, $R^2$ is $-NR^6R^7$, $R^3$, $R^4$ and $R^5$ each are a methyl group, $R^6$ and $R^7$, which may be the same or different from each other, represent a member selected from the group consisting of hydrogen, alkyl groups having from 1 to 20 carbon atoms and alkylene groups having from 1 to 20 carbon atoms, the unsubstituted phenyl group and phenyl substituted by $C_{1-3}$-alkyl, $C_{1-3}$-alkoxy, halogen or trifluoromethyl, and the benzyl group, l is zero and m is 1.

4. O-Carbamoyl-alkanediol-phospholipids as claimed in claim 1, wherein $R^2$ is $-NR^6R^7$, $R^3$, $R^4$ and $R^5$ each are a methyl group, $R^6$ and $R^7$, which may be the same or different from each other, are members selected from the group consisting of hydrogen, alkyl groups having from 1 to 20 carbon atoms and alkylene groups having from 1 to 20 carbon atoms, the unsubstituted phenyl group, phenyl substituted by $C_{1-3}$-alkyl, $C_{1-3}$-alkoxy, halogen or trifluoromethyl, and the benzyl group, and l and m both are 1.

5. O-Carbamoyl-alkanediol-phospholipids as claimed in claim 1, wherein $R^1$ is a member selected from the group consisting of the straight chain and branched chain alkyl groups having from 10 to 20 carbon atoms and the straight chain and the branched chain alkylene groups having from 10 to 20 carbon atoms, $R^2$ is $-NR^6R^7$, $R^3$, $R^4$ and $R^5$ each are a methyl group, $R^6$ and $R^7$, which may be the same or different from each other, are a member selected from the group consisting of hydrogen, alkyl groups having from 1 to 20 carbon atoms and alkylene groups having from 1 to 20 carbon atoms, the unsubstituted phenyl group, phenyl substituted by $C_{1-3}$-alkyl, $C_{1-3}$-alkoxy, halogen or trifluoromethyl, and the benzyl group, l is 1 and m is zero.

6. Process for the treatment of asthma in human beings wherein an O-acyl-alkanediol-phospholipid as claimed in claim 1 is administered to a human being suffering therefrom 2 to 3 times daily in a dose of 1 to 1000 mg. per dose.

* * * * *